United States Patent [19]

Temple

[11] 4,089,800
[45] May 16, 1978

[54] METHOD OF PREPARING MICROCAPSULES

[75] Inventor: Rodger G. Temple, Gibsonia, Pa.

[73] Assignee: PPG Industries, Inc., Pittsburgh, Pa.

[21] Appl. No.: 565,284

[22] Filed: Apr. 4, 1975

[51] Int. Cl.$^2$ .............................................. B01J 13/02
[52] U.S. Cl. .................................. 252/316; 71/64 F;
106/308 M; 106/312; 252/182; 252/426;
252/522; 260/2.5 B; 424/19; 424/33; 426/89
[58] Field of Search ........................................ 252/316

[56] References Cited

U.S. PATENT DOCUMENTS

| | | | |
|---|---|---|---|
| 3,558,507 | 1/1971 | Harbort | 252/316 |
| 3,664,963 | 5/1972 | Pasin | 252/316 |
| 3,669,899 | 6/1972 | Vassiliades et al. | 252/316 |
| 3,691,090 | 9/1972 | Kitajima et al. | 252/316 |
| 3,784,391 | 1/1974 | Kruse et al. | 252/316 X |

*Primary Examiner*—Richard D. Lovering
*Attorney, Agent, or Firm*—Charles R. Wilson; Frank J. Troy

[57] ABSTRACT

Void-containing microcapsules are prepared by a method featuring gellation of an organic polymer with the simultaneous precipitation of an organic liquid non-solvent. The method involves the preparation of a solution containing an organic polymer, a good solvent for the polymer and an organic liquid non-solvent which is miscible with the polymer solvent. The solution is then atomized into a bath containing a liquid which is miscible with the good polymer solvent but which is immiscible with the organic liquid non-solvent. The bath liquid extracts out the good polymer solvent, causing gellation of polymer around discrete droplets of the organic liquid non-solvent, which simultaneously precipitates out of the solution as the good polymer solvent is extracted, thereby producing microcapsules having encapsulated therein the non-solvent. The organic liquid non-solvent can then be removed as by evaporation to provide void-containing microcapsules. These void-containing microcapsules may be employed as opacifying agents. In addition to producing void-containing microcapsules, this method can be utilized to produce microcapsules in which pigments are entrapped in the voids or the polymeric walls of the microcapsules or in which certain non-solvents which serve a secondary function remain entrapped in the microcapsules. Such non-solvents include, for instance, vitamins, minerals, biocides, perfumes, chemical reactants, fertilizers, and the like.

11 Claims, No Drawings

METHOD OF PREPARING MICROCAPSULES

BACKGROUND OF THE INVENTION

The production of microcapsules by spray-drying techniques (i.e., atomization) is known in the art. Thus, it has been long known that solutions of polymeric alcohol xanthates, such as cellulose, starch, amylose, dextran, sugar, polyvinyl alcohol, polyallyl alcohol, etc., can be converted into regenerated polymeric alcohols in the form of small, hollow spheres by spray drying at a temperature sufficient to effect a decomposition of the xanthate. The solutions which are spray dried may be the ordinary caustic-containing solutions. The presence of caustic tends to accelerate the decomposition of the xanthate during the spray drying, but has the disadvantage of tending to depolymerize the polymeric alcohol. If the solution of polymeric alcohol xanthate is decausticized, as by dialysis, dilute acid or weak acid neutralization, cation exchange, anion exchange, etc., to a pH of less than about 13 prior to spray drying, the hollow spherical particles of regenerated polymeric alcohols which are produced are contaminated with less by-product materials and do not contain excess alkali, which tends to degrade the polymers. The xanthate solutions, either in the caustic or decausticized form, may be spray dried to produce hollow spheres of the xanthate. The hollow spheres of the xanthate or the regenerated alcohol are washed, preferably with acid, to remove alkali and by-products.

More recently, other methods of producing void-containing microcapsules by atomizaton have been proposed. One such method is disclosed in copending application Ser. No. 346,391, filed Mar. 30, 1973 and now abandoned, in the names of Simon Babil and James A. Claar. As disclosed in the copending application, a polymer solution consisting of an organic polymer, a volatile solvent for the polymer and a lower volatility non-solvent for the polymer which is miscible with the solvent or a polymer emulsion consisting of an organic polymer, a volatile solvent for the polymer and a lower volatility non-solvent which is immiscible with the solvent are atomized at a sufficient temperature and pressure to volatilize off the solvent to produce multicellular microcapsules having encapsulated therein the non-solvent, following which the non-solvent is removed by evaporation to produce void-containing multicellular microcapsules.

While the above-mentioned prior art methods of preparing void-containing microcapsules have certain advantages, they possess a number of serious disadvantages which materially limit their commercial acceptability. Thus, for example, in the early prior art as exemplified by the use of polymeric alcohol xanthate solutions, a considerable number of process steps were involved, such as decausticizing, washing the microcapsules to remove alkali and by-products, and collection and subsequent utilization of the microcapsules which often involves considerable handling. Even in the more recent prior art method as exemplified by the aforementioned copending application, certain disadvantages remain. Thus, for example, in the method of the copending application, it is necessary to select polymer solvents having sufficient volatility to be volatilized at the operating conditions of the atomizer apparatus. Further, the apparatus employed in the method is somewhat extensive and includes the necessity for a microcapsule collection chamber and, finally, the problems of handling the microcapsules for subsequent utilization remain.

DESCRIPTION OF THE INVENTION

This invention relates to a method of preparing microcapsules by a simplified process which eliminates or at least substantially minimizes many of the disadvantages of prior methods. The process, which is capable of producing void-containing microcapsules having an average diameter of from about 0.1 micron to about 250 microns involves preparing a solution containing an organic polymer, a good solvent for the polymer and an organic liquid non-solvent which is miscible with the polymer solvent. The solution is then atomized into a bath containing a liquid which is miscible with the polymer solvent, but which is immiscible with the non-solvent. The bath liquid extracts the good solvent from the polymer solution, causing gellation of the polymer particles around discrete droplets of the non-solvent, which are simultaneously precipitated out of the solution, thereby forming microcapsules having encapsulated therein droplets of the organic liquid non-solvent. The non-solvent can then be removed from the microcapsules as by evaporation to produce void-containing microcapsules.

The method of the present invention distinguishes over that used in the art in that after the atomization process the good polymer solvent is extracted from the polymer solution by the liquid of the bath into which the polymer solution is atomized, causing particles of the polymer to gel around discrete droplets of the organic liquid non-solvent which are simultaneously precipitated out of the solution to produce microcapsules having encapsulated therein droplets of the non-solvent, following which the non-solvent can be removed by evaporation to produce void-containing microcapsules.

The unique method of this invention has several advantages. Thus, both the method of preparation and apparatus utilized to carry out the method are greatly simplified, resulting in a substantial reduction in processing and equipment costs. The ingredients making up the polymer solution can be selected to permit atomization of the solution into a bath containing water, thereby providing for simplified solvent reclamation and reduced pollution of the ambient atmosphere. The ability to atomize into water is of additional advantage in that the microcapsules which form therein are easy to isolate. Finally, atomization into water reduces the need for complex collecting apparatus.

The microcapsules produced by the method of the invention possess several advantages. Thus, for example, they are less costly to prepare; they have a substantially uniform particle size distribution; they can be employed as flatting, texturing, and opacifying agents; and they can be employed for packaging or encapsulating biocides, herbicides, perfumes, fertilizers, medicaments, and the like.

The organic polymers employed herein may be of the thermoplastic or thermosetting type.

Thermoplastic resins which may be employed in the practice of this invention are well-known in the art.

Examples of thermoplastic resins which may be used include cellulose derivatives (e.g., ethyl cellulose, nitrocellulose, cellulose acetate, cellulose propionate and cellulose acetate butyrate); acrylic resins (e.g., homopolymers and copolymers with each other or with other monomers of esters, acids or other monomers containing an acrylyl or substituted acrylyl group, such as methyl methacrylate, ethyl acrylate, ethyl methacrylate, butyl acrylate, butyl methacrylate, acrylonitrile, acrylic acid and methacrylic acid); polyolefins (e.g.,) polyethylene and polypropylene); polyamides; polycarbonates; polystyrene; copolymers of styrene and other vinyl monomers, such as acrylonitrile; vinyl polymers, such as homopolymers or copolymers of vinyl acetate, vinyl alcohol, vinyl chloride and vinyl butyral; homopolymers and copolymers of dienes, such as polybutadiene, butadiene-styrene copolymers and butadiene acrylonitrile copolymers.

A preferred group of thermoplastic polymers are copolymers of acrylates, such as 2-ethylhexyl acrylate, and/or methacrylates, such as methyl methacrylate, with up to 50 percent of a comonomer, such as dibutyl maleate or fumarate, butyl glycidyl maleate or fumarate and glycidyl methacrylate. These thermoplastic polymers may be prepared in or dissolved in a solvent, such as benzene, toluene, butanol, acetone, xylene, or the like.

Graft copolymers or block copolymers may also be used as the thermoplastic resin. Such copolymers possess segmental periodicity, i.e., they contain continuous sequences of one monomer that are not governed by statistical distribution. They may be formed by methods known in the art, such as by polymerizing one or more monomers in the presence of an appropriate preformed polymer and catalyst. The preparation of graft copolymers is described, for example, in U.S. Pat. No. 3,232,903. The preformed polymer may be, for example, a polymeric ester of acrylic acid or acrylic acid formed with an alcohol having 4 to 18 carbon atoms, or of mixtures of such esters with esters of methacrylic acid or acrylic acid formed with alcohols having one to 5 carbon atoms. Monomers which may be polymerized in the presence of the preformed polymer include vinyl esters of fatty acids, esters of acrylic acid or methacrylic acid, and various other monomers copolymerizable with the preformed polymer. Some specific examples include: methyl methacrylate, ethyl acrylate, butyl methacrylate, acrylonitrile, acrylamide, styrene, acrylic acid, methacrylic acid, maleic anhydride and hydroxyalkyl acrylates or methacrylates, such as B-hydroxyethyl methacrylate.

Mixtures of two or more thermoplastic resins may also be used in this invention. Thus, for example, when a graft copolymer is prepared as described above, there is generally obtained a mixture of a graft copolymer comprising grafts of the polymerized monomer on the prepolymer, and a homopolymer of the monomer (or a copolymer if two or more different monomers are employed). This mixture of polymers may be used as such in the practice of this invention, or it may be separated into its component parts and either the graft copolymer or homopolymer used alone.

The thermosetting resins which may be used in the practice of this invention include those well-known in the art. Such resins are curable to a crosslinked thermoset condition by the use of either heat and/or a curing catalyst.

One preferred group of thermosetting resins which may be used in the practice of this invention are interpolymers of hydroxyl esters of ethylenically-unsaturated monomer, usually admixed with a crosslinking agent therefor, such as an aminoplast resin. Interpolymers of hydroxyl esters of unsaturated acids with at least one other polymerizable ethylenically-unsaturated monomer are prepared by interpolymerizing a hydroxyalkyl ester of an ethylenically-unsaturated carboxylic acid and at least one other ethylenically unsaturated monomer copolymerizable therewith. In many cases, more than one hydroxyalkyl ester is included in the interpolymer and generally several monomers, in addition to the hydroxyalkyl ester or esters, are employed. These interpolymers are produced in a manner well known in the art, using conventional procedures utilizing free radical catalysts or other mechanisms.

Preferred monomer systems used to produce these interpolymers are those containing hydroxyalkyl esters in which the alkyl group has up to about 12 carbon atoms. Especially preferred esters are acrylic acid and methacrylic acid esters of glycol and 1,2-propylene glycol, i.e., hydroxyethyl acrylate and methacrylate, hydroxypropyl acrylate and methacrylate. Combinations of these esters are also widely used. However, there may also be employed similar esters of other unsaturated acids, for example, ethacrylic acid, crotonic acid, and similar acids having up to about 6 carbon atoms, as well as esters containing hydroxyalkyl radicals, such as hydroxybutyl esters and hydroxylauryl esters.

The monomer or monomers with which the hydroxyalkyl ester is interpolymerized can be any ethylenic compound copolymerizable with the ester, the polymerization taking place through the ethylenically-unsaturated linkages. Preferred comonomers are alkyl esters of ethylenically-unsaturated carboxylic acids of vinyl aromatic hydrocarbons, or both. Among these preferred comonomers are the ethyl, methyl, propyl, butyl, hexyl, ethylhexyl, and lauryl acrylates and methacrylates, as well as similar esters having up to 20 carbon atoms in the alkyl group. Among the vinyl aromatic hydrocarbons generally utilized are styrene and alpha-alkyl styrene and vinyl toluene. Other useful monomers include monoolefinic and diolefinic hydrocarbons, halogenated monoolefinic and diolefinic hydrocarbons, unsaturated esters of organic and inorganic acids, esters of saturated acids, nitriles, unsaturated acids, and the like. Examples of such other monomers include 1,3-butadiene, vinyl butyrate, vinyl acetate, dimethyl maleate, acrylonitrile, methacrylonitrile, acrylic acid, methacrylic acid, and the like.

Crosslinking agents for interpolymers of hydroxyalkyl esters are materials which contain functional groups reactive with the hydroxyl groups of the interpolymer. Examples of such reactive materials include polyisocyanates, such as toluene diisocyanate and isocyanato-containing polymeric products; aminoplast resins, such as hexa(methoxymethyl)melamine and others described hereinafter; epoxy resins, such as polyglycidyl ethers of bisphenol A, and others, e.g., silicone resins.

Another preferred group of thermosetting resins which may be used in the practice of this invention are admixtures of alkyd resins, which may also be used with crosslinking agents therefor, such as aminoplast resins. Alkyd resins are obtained by the condensation of a polyhydric alcohol and a polycarboxylic acid. Any of the oil-modified or oil-free alkyd resins known in the art can be utilized.

Further details for the preparation of alkyd resins are described in the book entitled "ORGANIC COATING TECHNOLOGY", Volume 1, by Henry F. Payne, published by John Wiley & Sons (1954), Chapter 7.

Crosslinking agents for the alkyd resins include those materials which contain functional groups reactive with the hydroxyl groups of the alkyd, examples of which have been previously described in relation to crosslinking agents for interpolymers of hydroxyalkyl esters. The preferred crosslinking agents are aminoplast resins which will be more fully described hereinafter. Various proportions of alkyd resin and aminoplast resin crosslinking agent may be employed in the practice of this invention. For example, the aminoplast resin may constitute from about 5 to about 50 percent by weight of the mixture of the two resins although this ratio is not critical. The blend of the alkyd resin and the aminoplast resin may also include various added vehicular agents such as plasticizers, represented by epoxidized oils, so-called chemical plasticizers, such as triphenyl phosphate, tricresyl phosphate, dicyclohexyl phthalate, butylbenzyl phthalate, and others. Of couse, it is understood that aminoplast resins may be employed alone.

Aminoplast resins which are the preferred crosslinking agent for interpolymers of hydroxyl esters of unsaturated acids and for alkyd resins are derived from the reaction of a compound containing a plurality of $NH_2$-groups (e.g., urea, melamine, acetoguanamine or benzoguanamine) with an aldehyde (e.g., formaldehyde). In preparing aminoplasts, the aldehyde or its equivalent is usually dissolved in an alkanol, such as butyl alcohol, and at least a part of the N-methylol groups on the aminoplast are converted into N-oxyalkyl groups. It is preferred that the alkyl groups be butyl, i.e., that the curing agent be a butylated aminoplast.

Also suitable are amine-aldehyde condensation products of melamine, such as hexamethoxymethyl melamine, hexakis(methoxymethyl)melamine, ethoxymethoxymethyl melamine, hexylated methylated methylolmelamine and the like.

Further information as to the preparation and characteristics of aminoplast resins are contained in the aforementioned book entitled "ORGANIC COATING TECHNOLOGY", Chapter 8, pages 326–350.

Examples of thermosetting resin compositions comprising mixtures of an interpolymer of a hydroxyalkyl ester and an aminoplast resin are further described in U.S. Pat. No. 2,681,897; and further details for the preparation of aminoplast resins and alkyd resins which may be employed are described in U.S. Pat. No. 3,113,117.

Another group of thermosetting resins which may be used are carboxylic acid amide interpolymers of the type disclosed in U.S. Pat. Nos. 3,307,963 and 3,118,853. These interpolymers are prepared by forming an interpolymer of an unsaturated carboxylic acid amine, such as acrylamide or methacrylamide, with at least one other polymerizable ethylenically-unsaturated monomer, and then reacting the interpolymer with an aldehyde, such as formaldehyde, in the presence of an alcohol, such as butanol.

The aldehyde reacts with amide groups to form methylol groups and the butanol or other alcohol causes etherification so that at least some of the methylol groups are converted to groups of the structure:

$$-ROR_1$$

wherein R is a saturated lower aliphatic hydrocarbon radical derived from the aldehyde radical derived by removing the hydroxyl group from the alcohol.

It is desirable that at least about 50 percent of the methylol groups be etherified since compositions having less than about 50 percent of the methylol groups etherified will tend to be unstable and subject to gelation.

Any polymerizable monomeric compound containing at least one $CH_2=C<$ group may be polymerized with the unsaturated carboxylic acid amide. Examples of such monomers include styrene, isobutylene, vinyl chloride, vinylidene chloride, vinyl acetate, methyl methacrylate, ethyl acrylate, acrylonitrile, methacrylic acid, etc.

The preparation of the amide interpolymer is described in detail in U.S. Pat. Nos. 2,870,116 and 2,870,117.

Aldehyde-modified and etherified amide interpolymers can also be produced by first reacting the unsaturated amide with an aldehyde and, if desired, an alcohol, to form an N-alkylol or an N-alkoxyalkyl-substituted amide. The N-substituted amide is then interpolymerized with the other monomer or monomers as described above, thereby producing interpolymers having the aforesaid recurrent groups without the need for further reaction. Such a method utilizing N-alkoxyalkyl-substituted amides is described in U.S. Pat. No. 3,079,434.

Other thermosetting resin compositions which may be used include ethylenically unsaturated polyester resins obtained by the condensation of a glycol, such as ethylene glycol, propylene glycol, etc., and a polycarboxylic acid, such as maleic acid, fumaric acid, etc., in combination with a vinylidene monomer such as styrene, vinyl toluene, etc.; and the epoxy resins such as obtained by the combination of bisphenol and epichlorohydrin (e.g., Epon resins) in combination with a curing catalyst such as a polyamine (e.g., ethylene diamine).

Mixtures of two or more thermosetting resins may also be employed, as can mixtures of thermoplastic and thermosetting resins.

As pointed out hereinabove, these polymers may be blended or admixed with other curing agents, crosslinking agents or other reactive materials, depending on the desired results. It will be observed that if a thermosetting polymer is employed, that it may be cured after the microcapsule is formed or the polymer may be partially or wholly cured by regulating the temperature at which the atomization is carried out.

As indicated previously, the production of microcapsules by the method of this invention involves atomizing a solution containing an organic polymer, a good solvent for the polymer and an organic liquid non-solvent which is miscible with the polymer solvent into a bath containing a liquid which is miscible with the polymer solvent but which is immiscible with the organic liquid non-solvent of the solution.

The major criteria for the solvent is that it be a good solvent for the particular polymer employed. In contrast to prior methods, it is not necessary that the polymer solvents utilized in the practice of this invention be more highly volatile (i.e., have a higher evaporation rate) than the non-solvent since the polymer solvent herein is removed from the solution by means of extraction by the bath liquid.

The solvents or solvent combinations employed herein will vary somewhat, depending on the particular resin utilized. For example, solvents which are suitable for use with interpolymers of hydroxyl esters of unsaturated acids and an aminoplast resin include xylene, benzene, toluene, amyl acetate, butyl acetate, butyl propionate, dibutyl phthalate, diethyl phthalate, ethylene glycol, diethyl ether, ethyl phenyl ether, diphenyl ether, butyl benzyl ether, etc. When the thermosetting resin composition comprises an alkyd resin and an aminoplast resin, suitable solvents include alcohols containing from about 3 to about 8 carbon atoms, such as propyl alcohol, isopropyl alcohol, butyl alcohol, amyl alcohol, nonyl alcohol, octyl alcohol, etc.; aromatic hydrocarbons such as xylene or toluene; ketones such as methyl ethyl ketone, methyl isobutyl ketone, cyclohexanone, isophorone, etc.; esters, such as isopropyl acetate, butyl acetate, amyl acetate, nonyl acetate; phosphates, such as tributyl phosphate; and chlorinated hydrocarbons, such as methylene chloride. Combinations of certain solvents are likewise suitable in some instances.

It will be noted that water may also be employed as a solvent. When thermoplastic polymers are utilized, methylene chloride, and acetone have been found to be particularly useful.

The basic requirements for the organic liquid non-solvent are that it be a non-solvent for the polymer employed; that it be miscible or at least substantially miscible with the solvent to form a true solution or a colloidal near solution; that it be sufficiently low in volatility (i.e., evaporation rate) to remain in the system during atomization; and that it be present in an amount sufficient to produce upon drying or evaporation substantially closed cell void-containing microcapsules.

The non-solvent is a non-solvent for the polymer and it is preferable that the non-solvent be volatile or at least volatilizable so that the non-solvent can be readily removed from the microcapsules when desired. Non-solvents of very high boiling points are useful, for example, those having boiling points up to the melting point of the coalescable polymer or even higher may be used. Sublimable solids can also be used under appropriate conditions. While essentially non-volatile non-solvents may be useful, they require removal by extraction or similar means which require additional processing and thus are relatively undesirable. It will be understood that each polymer will have its own series of usable and optimal non-solvents. Those most suited for any particular system may be readily selected by the skilled artisan on the basis of the known physical properties of liquids and polymers. One method which may be employed in selecting the optimum non-solvent for a particular resin system is the method of Hansen ["THE THREE DIMENSIONAL SOLUBILITY PARAMETER AND SOLVENT DIFFUSION COEFFICIENT AND THEIR IMPORTANCE IN SURFACE COATING FORMATION". Copenhagen, Danish Technical Press (1967)] to determine liquids which will not solubilize the particular polymer selected. Once these liquids are ascertained, the solubility parameters found in the work of Hoy ("TABLES OF SOLUBILITY PARAMETERS", Union Carbide Corporation, South Charleston, W. Va., May 31, 1967) may be utilized. The work of Hoy tabulates the relative evaporation rates of liquids wherein a non-solvent can be selected which has a low enough volatility to remain in the coating long enough to form voids before evaporating.

An example of utilizing the foregoing method can be illustrated by selecting poly(vinylacetate) as the polymer system. The Hansen parameters for this system are $d$ 9.3, $p$ 5.0, $h$ 4.0 and $r$ 4.9. Thus, the only practical materials outside this large solubility sphere are the water-soluble liquids, such as glycols, alcohols, amines, etc., and the non-polar aliphatics, such as hexane, cyclohexane, carbon tetrachloride, etc. Since water-solubles are not preferred, the non-polar aliphatics would be selected. Referring to the Hoy tabulation of relative evaporation rates (which is based on butyl acetate as 100), it can be seen that the aliphatic hydrocarbons, such as decane (boiling point 172° C., relative evaporation rate 12.96); undecane (boiling point 193° C., relative evaporation rate 4.41) and dodecane (boiling point 214° C., relative evaporation rate 1.42) are all reasonable non-solvents for the poly(vinylacetate) resins system. A commercially-available liquid non-solvent which will simulate these pure, commercially-available compounds is usually chosen and utilized.

Some examples of non-solvents which have been found particularly useful are odorless mineral spirits, high flash aliphatic naphtha, naphthenic mineral oil, neat's foot oil, pin oil, and the like. The odorless aliphatic mineral spirits and high flash aliphatic naphthas generally have a boiling point range of from about 300° F. to about 600° F., preferably from about 400° F. to 550° F. Typical mixed aliphatic-aromatic compounds which may be employed as non-solvents are phenyl cyclohexane, triethyl benzene, phenyl propane, and the like. Various other compounds may be employed as non-solvents, such as dicyclohexyl amine, isoamyl bromide, trichloropropane, methyl benzyl ketone, allyl butyrate and the like. Some of the preferred non-solvents include water, n-heptane, ethanol and VM&P naphthas.

The weight ratio of the non-solvent to the solvent generally falls in the range of from about 1:1 to about 1:100 in solution compositions. This non-solvent to solvent ratio may be varied widely, and such ratios are dependent upon the strength of the solvent, the resin solubility, the size of the voids and other desired results. However, for purposes of the present invention, the preferred ratio is from about 1:1 to about 1:20, and the most preferred range is from 1:6 to about 1:20.

The basic requirement for the bath into which the above-described solution is atomized is that it contain a liquid which is miscible with the good polymer solvent and immiscible with the non-solvent so that it will extract the polymer solvent from the solution. As will be apparent, the bath liquid must not be a solvent for the polymer if microcapsules are to be produced. The selection of an appropriate bath liquid is well within the skill of the art. Thus, appropriate bath liquids can be selected by the skilled artisan on the basis of the known physical properties of liquids and polymers. A preferred bath liquid is water.

As indicated above, in producing void-containing microcapsules by the method of this invention, the liquid non-solvent is removed as by evaporation. The method of this invention is also applicable to producing microcapsules in which the non-solvent can perform a secondary function in addition to the formation of the microcapsule and remains entrapped in the polymeric microcapsule until performance of the additional function is desired. Thus, the non-solvent can be encapsulated in the polymeric microcapsules and remain entrapped until the wall is ruptured, punctured or worn away, or until it diffuses through the wall. The polymer of the polymer wall may be selected to that it is biodegradable, and thus slowly releases the entrapped non-solvent. Accordingly, in some instances the non-solvent may be a solid, liquid or a gas, depending upon the function desired.

For example, the non-solvent may be a medicament; food; vitamin; mineral; biocide, such as insecticides; chemical reactant, such as curing agents, catalysts, and the like; herbicide, fungicide, mildewcide, and the like, as well as perfumes, odorants, fertilizers, repellants, and the like.

In addition, various adjuvants may be incorporated in the microcapsules of this invention; for example, conventional pigments may be incorporated. These include titanium dioxide, encapsulated aluminum silica, lead silica chromate, carbon black, talc, barium sulfate, and the like, as well as combinations of these and similar pigments. Colored pigments such as cadmium red, cadmium yellow, phthalocyanine blue, phthalocyanine green, chrome green, toluidine red, hydrated iron oxide, and the like may be included if desired. Also, other adjuvants may be incorporated, such as dispersing agents, surface-active agents, adhesion promoting agents, melting agents, flow agents, anti-oxidants, chemical reactants and the like.

The pigments defined hereinabove may be incorporated, either in the polymeric material or the non-solvent. If the pigment has been dispersed in the non-solvent when the non-solvent is evaporated, the pigment will remain entrapped in the voids; while, on the other hand, if the pigment has been incorporated into the polymeric material, the pigment will then remain in the walls of the microcapsules. The compositions employed in the practice of this invention may be atomized at a solids content of from about 0.5 to 35 percent by weight, based on the weight of the total composition, or higher when desired. It will be noted that the solids content will depend on the nature of the atomization apparatus, the molecular weight of the polymer, the strength of the solvents employed, the viscosity of the polymer and the temperature at which the composition is atomized. A solids content of from about 2 percent to about 20 percent by weight, based on weight of total composition, is preferred.

The viscosity of the composition to be atomized should be such as to permit the formation of individual particles rather than the formation of strings of polymer, which is indicative of high viscosity. For this reason, it is usually desirable that the molecular weight of the polymer be less than about 140,000 and preferably less than 100,000 and, most preferably, less than 90,000.

The apparatus employed in atomizing the compositions or solutions employed in the practice of this invention may be any standard liquid atomizing device such as the pneumatic, air, airless, hydraulic, centrifugal, electrostatic, or ultrasonic spraying devices commonly employed in the coatings industry. It is only necessary that the device or apparatus be capable of atomization to such a degree as to provide the microcapsules described herein.

Atomizers or spraying devices employed in the coatings industry are well known. For example, air spraying is typically employed. Air spraying operates on a principal which involves extruding a stream of liquid material from a nozzle (e.g., a spray gun) at relatively low pressure and then impacting the stream with a higher pressure stream of air to atomize the liquid into a spray of fine droplets. The size of the droplets is controlled by well known spraying parameters including but not exclusively, air pressure, solids, flow rate of liquid into atomizer, size of atomizer orifice and the like.

It will be noted that the composition employed in the practice of this invention can be heated if desired. However, it is preferred that the composition be sprayed at room temperature. However, if a thermosetting polymeric composition is employed, then heating may be desired to provide for a partial cure or fusing of the polymer. It is also desirable that the non-solvent evaporate at room or ambient temperature; however, in some instances the microcapsules may be heated slightly in order to drive off or vaporize the non-solvent.

The diameter of the microcapsules produced may range from as low as 0.1 to as high as 250 microns. However, it is preferred that the microcapsules herein have an average particle diameter of from about 0.5 to about 25 microns, and the most preferred range is from about 0.5 to about 1 micron.

The size of the voids in the microcapsules may be varied considerably depending on desired properties and may approach the maximum particle diameter above but most will have a diameter of from about 0.1 to about 10 microns, the preferred diameter being from 0.5 to about 4 microns, and the most preferred range being from about 0.5 to about 1 micron.

Set forth below are several specific embodiments of the preparation of the void-containing multicellular microcapsules of this invention. These embodiments are illustrative and are not to be construed as limiting the invention. All parts and percentages are based on weight unless otherwise indicated.

EXAMPLE 1

A solution was prepared by dissolving 45 grams of polymethyl methacrylate in 850 grams of acetone, then 200 grams of a non-solvent, n-heptane, were added slowly while the solution was maintained under constant agitation. The solution was then sprayed at room temperature utilizing a siphon spray gun into a water bath maintained under agitation with a Cowless mixer. The non-solvent was then evaporated to provide void-containing microcapsules having a particle size of from about 0.1 micron to about 250 microns in diameter.

EXAMPLE 2

In this Example, Example 1 was repeated except that the solution contained 45 grams polymethyl methacrylate, 900 grams acetone solvent and 100 grams n-heptane non-solvent. The solution was sprayed into a water bath utilizing conditions similar to those of Example 1 and upon evaporation of the non-solvent void-containing microcapsules were produced.

EXAMPLE 3

A solution was prepared in accordance with the procedure of Examples 1 and 2. The solution consisted of 45 grams of polyethyl methacrylate, 850 grams of acetone (solvent) and 200 grams of n-heptane (non-solvent). This solution was then sprayed in a conventional spray booth into a flowing water curtain. The water extracted the polymer solvent, thereby producing microcapsules containing droplets of the non-solvent. These microcapsules were collected in a receptacle into which the water-curtain flowed. Upon drying of the microcapsules, the non-solvent was evaporated to produce void-containing microcapsules.

EXAMPLE 4

In this example, Example 3 was repeated except that the polymer solution consisted of 45 grams of polymethyl methacrylate, 900 grams of diacetone alcohol (a low volatility solvent) and 200 grams of n-heptane (non-solvent). This example, also produced void-containing microcapsules as in Example 3 and in greater yield than in Example 3.

EXAMPLE 5

A solution consisting of 45 grams of polymethyl methacrylate, 900 grams of acetone (solvent) and 200 grams of n-heptane (non-solvent) was prepared as in Examples 1–4. However, in this example, the solution was sprayed into the water bath utilizing a standard electrostatic spraying system operated at 20–40 KV and a distance of from 1–3 feet. As in the previous examples, the water extracted the polymer solvent from solution, causing the formation of microcapsules containing droplets of the non-solvent. As in the previous examples, drying of these microcapsules evaporated the non-solvent to produce void-containing microcapsules.

According to the provisions of the Patent Statutes, there are described above the invention and what are now considered to be its best embodiments. However, within the scope of the appended claims, it to be understood that the invention can be practiced otherwise than as specifically described.

I claim:

1. A method of preparing void-containing microcapsules having a particle diameter of from about 0.1 micron to about 250 microns which comprises the steps of:
    (A) preparing a solution containing thermoplastic or thermosetting organic polymer, a good solvent for the polymer and an organic liquid non-solvent and wherein the weight ratio of non-solvent to solvent is from about 1:1 to about 1:100;
    (B) atomizing said solution into a bath containing water which is miscible with the good solvent and immiscible with the non-solvent whereby the good solvent is extracted from the solution, thereby causing gellation of the polymer around discrete droplets of the non-solvent, thereby forming microcapsules containing droplets of said liquid non-solvent; and
    (C) evaporating said liquid non-solvent from said microcapsules to produce void-containing microcapsules.

2. The method of claim 1 wherein the organic polymer is a thermoplastic polymer.

3. The method of claim 2, wherein the thermoplastic polymer is a thermoplastic resin selected from the group consisting of cellulose derivatives, acrylic resins, polyolefins, polyamides, and polycarbonates.

4. The method of claim 2 wherein the thermoplastic polymer is selected from the group consisting of polyalkylacrylates, polyalkylmethacrylates and mixtures thereof.

5. The method of claim 3 wherein the thermoplastic polymer is polymethylmethacrylate.

6. The method of claim 1 wherein the organic polymer is a thermosetting polymer.

7. The method of claim 6 wherein the thermosetting resin is selected from the group consisting of alkyd resins, carboxylic acid-amide interpolymers, and interpolymers of hydroxyl esters of ethylenically-unsaturated acids with at least one other polymerizable ethylenically-unsaturated monomer.

8. The method of claim 1 wherein the solution contains polymethyl methacrylate, acetone and n-heptane.

9. The method of claim 1 wherein the solution has a non-solvent to solvent weight ratio of from about 1:1 to about 1:20.

10. The method of claim 1 wherein the solution has pigment incorporated in the polymer solvent.

11. The method of claim 1 wherein the solution has pigment incorporated in the non-solvent.

* * * * *